(12) United States Patent
Elrod

(10) Patent No.: US 6,200,795 B1
(45) Date of Patent: Mar. 13, 2001

(54) POLYPEPTIDES HAVING UROPORPHYRINOGEN DECARBOXYLASE ACTIVITY AND NUCLEIC ACIDS ENCODING SAME

(75) Inventor: Susan L. Elrod, San Luis Obispo, CA (US)

(73) Assignee: Novo Nordisk Biotech, Inc., Davis, CA (US)

( * ) Notice: Subject to any disclaimer, the term of this patent is extended or adjusted under 35 U.S.C. 154(b) by 0 days.

(21) Appl. No.: 09/193,069

(22) Filed: Nov. 16, 1998

Related U.S. Application Data
(60) Provisional application No. 60/065,901, filed on Nov. 17, 1997.

(51) Int. Cl.$^7$ .................................................... C12N 9/88
(52) U.S. Cl. ..................... 435/232; 435/69.1; 435/183; 435/41; 530/350; 536/23.1; 536/23.2; 536/23.5
(58) Field of Search ...................... 435/183, 69.1, 435/41, 232; 536/23.1, 23.2, 23.5; 530/350

(56) References Cited

FOREIGN PATENT DOCUMENTS
WO 93/19195    9/1993  (WO).

OTHER PUBLICATIONS
Gary et al., 1992, European Joournal of Biochemistry 205: 1011–1016.
Diflumeri et al., 1993, Yeast 9: 613–623.
Hansson & Hederstedt, 1992, Journal of Bacteriology 174: 8081–8093.
Nishimura et al., 1993, Gene 133 :109–113.
Kiel et al., 1992, DNA Seq. 2: 415–418.
Ineichen & Biel, 1995, Plant Physiology 108: 423.
Romeo et al., 1986, Journal of Biological Chem. 261: 9825–9831.
Wu et al., 1996, Mammalian Genome 7: 349–352.
Smith & Waterman, 1981, Nucleic Acids Research 10: 197–206.
Garey et al. (1992) Eur. J. Biochem. 205, 1011–1016, May 1992.*
Romeo et al. (1986) J. Biol. Chem. 261 (21), 9825–9831, Jul. 25, 1986.*
Wu et al. (1996) Mammal. Genome. 7, 349–352, May 1996.*
Romana et al. (1987) Nuc. Acid. Res. 15 (17), 7211–7212, Sep. 11, 1987.*

* cited by examiner

*Primary Examiner*—Rebecca E. Prouty
*Assistant Examiner*—Richard Hutson
(74) *Attorney, Agent, or Firm*—Robert L. Stames; Elias Lambiris Esq.; Steve Zealson Esq.

(57) ABSTRACT

The present invention relates to isolated polypeptides having uroporphyrinogen decarboxylase activity and isolated nucleic acid sequences encoding the polypeptides. The invention also relates to nucleic acid constructs, vectors, and host cells comprising the nucleic acid sequences as well as methods for producing and using the polypeptides.

17 Claims, 5 Drawing Sheets

|   |   |     |
|---|---|----:|
| 1   | ACACTATAAAAGAGCTATGACGTCGCATGCACGCGCGTACGCGTAAGCTTGGATCCTCTTTTA | 60 |
| 61  | GAGCGGCCGCCGAYTAGTGAGCTYGTCGACCCGGGAATTTGGCGTTGAAGGGCGCGGCGG | 120 |
| 121 | CACTGCGAGGCCGGGGGGTCATTCCCGTCATAGCCGTCGTTGTCGTTGTCGTTGTCGTTGTC | 180 |
| 181 | GTCGTTGCTGCGCGACGGARGAGGAATATCTCGGCTGCCAGTCCATCCAGAAAAATA | 240 |
| 241 | GGCGCGTTTGATGCTCTCCTCTCTTTGCCCGTCTCTTGTGGATGGAGCTGCCTTCGATATG | 300 |
| 301 | ACCGCAATCGCAGTCTCGTCGGGCCAATCGGGCGCTGCTTCGCTTCGCGACGTCGCGAATGAGTT | 360 |
| 361 | GCGCTGGAAAAAACCGAGCCCCTGCTCGCTTCGGCAGCTTTGATGAAGCTTCAAGCGATCG | 420 |
| 421 | TGTGCGGCTGATGTGGCAGGTGTGTAGCTTAGCTTAGCTGATGCTGGAATTGGCAGGGT | 480 |
| 481 | TAAGGTACCTTGCAGGTGTGGGCGGCACACTACCTAGCCTGAAGGTGAGCCGGATGTC | 540 |
| 541 | GGCTGTCAGGTGCCCCTCGCTTACCCTCGAGACCGAGCCCGAGCCCCTCGAAGCTTCCATCTTG | 600 |
| 601 | GCGGGGACCTTCCACCTCGAGACCGAGCCCGGAACAAGTCCACCTACCTGAACCATGGA | 660 |
|     |                                                      M E |     |
| 661 | AGAGCACTCATTCCCACCGCTCCAGAACGACTCCTGTTGAGGGCCGCATGGGTAAGTG | 720 |
|     | E H S F P P L Q N D L L R A A W |     |

Fig. 1A

```
721   AACGCTGACTTTTTCTTTCTTTTTCTTATTTTAAATTTCGTTTTGATT
781   TGTAGATATCCTTGGTTCAAAAAACGTTTGCTGACATGGCAAGCGGTCG                           840
                                                  G  Q  A  V
841   AACGGCCGCCCATCTGGGTGATGCGCAGGGTGAGGAGCACAGCCCGGCGCTCCTGCTGC                900
      E  R  P  P  I  W  V  M  R  Q
901   CCTCATGTGCAACACGCCGCTGACACCCGGTGCAGCTGGCCGTTACCTGCCCGAATACCA                960
                                   A  G  R  Y  L  P  E  Y  H
961   CGAAGCCAAGGGATCCCCGGACTTCTTCGAGTGCTGCAGGGACCCGGAGGTCGCATCCAC                1020
      E  A  K  G  S  R  D  F  F  E  C  C  R  D  P  E  V  A  S  T
1021  GCTGACATTGCAACCAATTGAACGCTATGCCGGCCTCGTTGATGCCGCCATCATCTTCTC                1080
      L  T  L  Q  P  I  E  R  Y  A  G  L  V  D  A  A  I  I  F  S
1081  GGACATCCTCGTGATCCCCCAGGCCATGGGAATGCTCGTTGAAATGGTCGACAAGAAAGG                1140
      D  I  L  V  I  P  Q  A  M  G  M  L  V  E  M  V  D  K  K  G
1141  CCCCCCACTTCCCCAATCCGGTGCAACGTGGCAAGGAGCTCGACTAGTCTACAAGGCTATCACCCTGACGAG    1200
      P  H  F  P  N  P  L  R  S  P  D  D  G  Q  Y  A  A  L  M  Q
1201  GCGCACCGTGCGACGTCGAGCTGGACTATGTCTACAAGGCTATCACCCTGACGAG                     1260
      R  T  V  D  V  A  T  E  L  D  Y  V  Y  K  A  I  T  L  T  R
1261  GAAGAAGCTGCAGGGTCGGGTGCCCCTGTTCTGCGGCTTCTGCGGGGCGCCGTGGACTTTGTT             1320
      K  K  L  Q  G  R  V  P  L  F  C  G  F  C  G  A  P  W  T  L  F
1321  CTGCTATATGGTTGAGGGTGGGGGAGACCAAGGCCCCTTCTGCAAAAGATCTCGGAGCTTTGTGTTGAGTA    1380
      C  Y  M  V  E  G  G  G  T  K  L  F  K  E  S  K  T  W  I  Y
1381  TAAGTATCCCGAGGAGACCAAGGCCCTTCTGCAAAAGATCTCGGAGCTTTGTGTTGAGTA                1440
      K  Y  P  E  E  T  K  A  L  L  Q  K  I  S  E  L  C  V  E  Y
```

Fig. 1B

```
1440        CCTCGCTCTCCAGTCAAGGCCGGGCCCAGTATGTACGAGCATTAAGCGACCCTCATT    1500
             L  A  L  Q  V  K  A  G  A  Q
1501        CTCCCTAGATCTTATGCTCTGATTGCCGTGCCAGATCATCCAAGTATTCGACTCGTGGGC   1560
                               I  Q  V  F  D  S  W  A
1561        CGGCGAGCTGTCGCCCTCTTCATTCAAGAAATTCTCACAGCCCTTATCTGGCTTACATTGC   1620
             G  E  L  S  P  S  S  F  K  K  F  S  Q  P  Y  L  A  Y  I  A
1621        CCAGCACCTCCCCCGCCAGGCTGAAGCAGAGATGGGTTTGGAACCCGTTCCCATGGTCGTGTT   1680
             Q  H  L  P  A  R  L  K  Q  M  G  L  E  P  V  P  M  V  V  F
1681        CCCCAAAGGCGCATGGTATGCCCTCGACGCTGCGTGCGACATGGGATACAACGTTGTCAG   1740
             P  K  G  A  W  Y  A  L  D  A  A  C  D  M  G  Y  N  V  V  S
1741        TCTGGACTGGCTCCACGATCCGGCCGATGCTGTCAAGGTCGTTGGCGACCGGCCAGTCGT   1800
             L  D  W  L  H  D  P  A  D  A  V  K  V  V  G  D  R  P  V  V
1801        TCTCCAGGAAACGCTGACCCCGGTTCTGTACGGCTGCCATGCTGCCATCACCGAGGC   1860
             L  Q  G  N  A  D  P  G  V  L  Y  G  S  H  A  A  I  T  E  A
1861        CGTGGCTGAGATGGTAAAGGGCTTTGGCTGGCCGGATCGGAAGAAGGGCTGGATTGTGAA   1920
             V  A  E  M  V  K  G  F  G  W  P  D  R  K  K  G  W  I  V  N
1921        CCTCGGGCATGGTGCCGTTCCCATCGCGCTTTCAACCGTGCCACCACTAACGGGTCAC   1980
             L  G  H
1981        AGGGATCACGCCATTCGTCAACCCGGACGACTTAAAATTCTTCTTTCAGGAGATCCACCG   2040
             G  I  T  P  F  V  N  P  D  D  L  K  F  F  F  Q  E  I  H  R
2041        CCTGACCAAGACGGATGGCCAATAGACAGTGAAACGCAATGTTGAGTTCGGAATGTCACGA   2100
             L  T  K  T  D  G  Q
2101        CATTCTGCTCAGCTCAGCATGTGTATTATTATCCGAGAGCGGAATGTATGGTACCGCGGA   2160
```

Fig. 1C

| | | |
|---|---|---|
| 2161 | TCTCCAATCCAACCACTCACATAGGATCTGCTGAGATGCAGTATTGCCCTGA | 2220 |
| 2221 | AGCCAGTCAGGGAGATCCTCGACTTTGATGTCGCCCATCTTACCAAGACAGAGTCCAGCT | 2280 |
| 2281 | GAGCTTGCCGCCAATGCTTCGGCAAAATGCCTGGCTCCCGGAATTCTCGACGAACACATC | 2340 |
| 2341 | GGCCGCCCCCAGCCGTCGTTCCCAGCCGTACTCATGGAGGTATTCGGCATCAGCCTGCAGCC | 2400 |
| 2401 | CAACGCTTTTGCAAGGCCCATGCGACGATATGCTTCCTGGAGTCCGTATAAGCCAAGGAG | 2460 |
| 2461 | TCTAGTGTCAAGGCAGATGCTCCAATACATACCTCAACATGTAGCCGTGATGATGGTCCCG | 2520 |
| 2521 | TCAAGCCCTGGTGTTCCTGTCAGTCTCAAGCAGCCAGTAACAGTCATCCGGATGCTCCCC | 2580 |
| 2581 | GACTCACCCATAAACGCCCAGGCAACCGGAGTTCCATCCTTGAGTCTGACACACATACTC | 2640 |
| 2641 | GGGAGCATCAACAGCGTTGCCCGCCACAACCGGCCTGCTCAGCCCCGTTCTCTCTCCA | 2700 |
| 2701 | ATATCCCATTCACTAAAGAGAAATACTCACTCCCGCCTTGATACTCGTCCGCTCCAGC | 2760 |
| 2761 | ACCAGCGCAACATCCTTCCGCACCCTGTCCCCATCCCCTGCGGCAGCACCTCA | 2820 |
| 2821 | GCGGACGCAGCAGGCAAATCCTCCACCCGAAACAGCCACTTGCCACAATACTCCCATTCC | 2880 |

Fig. 1D

2881 AGCTCGGSCGGGATACTCGGSGAMTTCTCCATCGCCACCCCGCGCAAGCAAGCCCTGC 2940
2941 CGCACCGTCTCGTGCAGCGAGCCCACGAAGAACTTCGTCATCGTCCCTCTCCCCGTT 3000
3001 CCTCTTCTCCTCCCATTTCCTCCACCTCCCCCCCTGNTGANAAAACGTTGTTGCATGGGCT 3060
3061 GGGGCCTTTGCCTCAGCATCAGCATCAGCATCGGNATCAGCAAGCGCAATACCC 3120
3121 TGAACCGCCGCAG 3133

Fig. 1E

SEQUENCE LISTING

```
<160> NUMBER OF SEQ ID NOS: 4

<210> SEQ ID NO 1
<211> LENGTH: 3133
<212> TYPE: DNA
<213> ORGANISM: Thielavia
<220> FEATURE:
<221> NAME/KEY: misc_feature
<222> LOCATION: (0)...(0)
<223> OTHER INFORMATION: n = a or c or g or t

<400> SEQUENCE: 1
acactataaa aagagctatg acgtcgcatg cacgcgtacg taagcttgga tcctctttta     60
gagcggccgc cgaytagtga gctygtcgac ccgggaattc ggcgttgaag ggcgcggcgg    120
cactgcgagg ccgggggggt cattcccgtc atagccgtcg ttgtcgttgt cgtcgttgtc    180
gtcgttgctg cgcgacggar gagggatctc ggctcggtgc cagctccatc cagaaaaata    240
ggcgcgtttg atgctctcct tctctttgcc cgtcttgtgg atggagctgc cttcgatatg    300
accgcaatcg cagtctgtcg gggccaatcg ggccgctgac gtcgacgtcg cgaatgagtt    360
gcgctggaaa aaaccgagcc ctgctcgctt cggcagcttt gatgaagctt caagcgatcg    420
tgtgcggctg atgtggctga tgcttagcta acccacccaa ccagtggaat tggcaggggt    480
taaggtacct tgcaggtgtg gcgcggcaca ctacctagcc tggaaggtga gccggatgtc    540
ggctgtcagg tgcccctcgc ttaccctccc tcaacatcaa ttgaattggc ttccatcttg    600
```

-continued

```
gcggggacc ttccacctcg agaccgagcc cggaacaagt ccacctacct gaaccatgga      660
agagcactca ttcccaccgc tccagaacga cctcctgttg agggccgcat ggggtaagtg      720
aacgctgact ttttcttctt tctttctttt cttttttctta ttttaaattt cgttttgatt    780
tgtagatatc cttggttcaa aaaacgtttg ctgacatggc aactgcaggc caagcggtcg     840
aacggccgcc catctgggtg atgcggcagg gtgaggagca cagcccggcg tcctcgctgc     900
cctcatgtgc aacacgccgc tgacacccgg tgcagctggc cgctacctgc ccgaatacca     960
cgaagccaag ggatcccgcg acttcttcga gtgctgcagg gacccggagg tcgcatccac    1020
gctgacattg caaccaattg aacgctatgc cggcctcgtt gatgccgcca tcatcttctc    1080
ggacatcctc gtgatccccc aggccatggg aatgctcgtg aaatggtcg acaagaargg     1140 cccccacttc cccaatccgc tgcgcagccc agacgacgga cagtacgccg cgctgatgca    1200
gcgcaccgtc gacgtggcaa cggagctcga ctatgtctac aaggctatca ccctgacgag    1260
gaagaagctg cagggtcggg tgcccctgtt cggcttctgc ggggcgccgt ggactttgtt    1320
ctgctatatg gttgagggtg ggggaccaa actgtttaag gaatcgaaga catgatttta    1380
taagtatccc gaggagacca aggccttct gcaaaagatc tcggagcttt gtgttgagta     1440
cctcgctctc caggtcaagg ccggcgccca ggtatgtacg agcattaagc gaccctcatt    1500
ctccctagat cttatgctga ttgatgcgtg ccagatcatc caagtattcg actcgtgggc    1560
cggcgagctg tcgccctctt cattcaagaa attctcacag ccttatctgg cttacattgc    1620
ccagcacctc cccgccaggc tgaagcagat gggtttggaa cccgttccca tggtcgtgtt    1680
ccccaaaggc gcatggtatg cgctcgacgc tgcgtgcgac atgggataca acgttgtcag    1740
tctggactgg ctccacgatc cggccgatgc tgtcaaggtc gttggcgacc ggccagtcgt    1800
tctccaggga aacgctgacc ccggcgttct gtacggctcg catgctgcca tcaccgaggc    1860
cgtggctgag atggtaaagg ctttggctg gccggatcgg aagaagggct ggattgtgaa     1920
cctcgggcat ggtgcgtttc ccatcgcgct ttcaaccgtg ccaccacact aacgggtcac    1980
agggatcacg ccattcgtca acccggacga cttaaaattc ttctttcagg agatccaccg    2040
cctgaccaag acgatggcc aatagcagtg aaacgcaatg ttgagttcgg aatgtcacga    2100
cattctgctc agctcagcat gtgtattatt atccgagagc ggaatgtatg gtaccgcgga    2160
tctccaatcc aaccactcac ataggatctc caacgctgct gagatgcagt attgccctga    2220
agccagtcag cgagatcctc gactttgatg tcgcccatct taccaagaca gagtccagct    2280
gagcttgccg ccaatgcttc ggcaaaatgc ctggctcccg gaattctcga cgaacacatc    2340
ggccgccccc cagccgtcgt tcccgtactc atggaggtat tcgcgcatca gcctgcagcc    2400
caacgctttt gcaaggccca tgcgacgata tgcttcctgg agtccgtata agccaaggag    2460
tctagtgtca aggcagatgc tccaatacat acctcaacat gtagcgtgat gatggtcccg    2520
tcaagccctg gtgttcctgt cagtctcaag cagccagtaa cagtcatccg gatgctcccc    2580
gactcaccca taaacgccca ggcaaccgga gttccatcct tgagtctgac acacatactc    2640
gggagcatca acagcgttgc cctgccacaa ccgcgcctgc tcagccccgt tctctctcca    2700
atatcccatt cactaaagag aaatactcac tcccgccgct tgatactcgt ccgctccagc    2760
accagcgcaa catcctcctt ccgcaccctg tcccaccgca tccctgcgg cagcacctca     2820 gcggacgcag caggcaaatc ctccacccga aacagccact tgccacaata ctcccattcc    2880
agctcggscg ggatactcgg sgamttctcc atcgccaccc cgcgcgcaag caagccctgc    2940
```

-continued

```
cgcaccgtct cgtgcagcga gcccacgaag aacttcgtca tcgtccctct cctccccgtt    3000
cctcttctcc tcccatttcc tccacctccc ccttgntgan aaaacgttgt tgcatgggct    3060
ggggcctttg cctcagcatc agcatcagca tcagcatcgg natcagcaag cgcaataccc    3120
tgaaccgccg cag                                                       3133
```

<210> SEQ ID NO 2
<211> LENGTH: 371
<212> TYPE: PRT
<213> ORGANISM: Thielavia

<400> SEQUENCE: 2

```
Met Glu Glu His Ser Phe Pro Pro Leu Gln Asn Asp Leu Leu Leu Arg
 1               5                  10                  15

Ala Ala Trp Gly Gln Ala Val Glu Arg Pro Pro Ile Trp Val Met Arg
             20                  25                  30

Gln Ala Gly Arg Tyr Leu Pro Glu Tyr His Glu Ala Lys Gly Ser Arg
         35                  40                  45

Asp Phe Phe Glu Cys Cys Arg Asp Pro Glu Val Ala Ser Thr Leu Thr
     50                  55                  60

Leu Gln Pro Ile Glu Arg Tyr Ala Gly Leu Val Asp Ala Ala Ile Ile
 65                  70                  75                  80

Phe Ser Asp Ile Leu Val Ile Pro Gln Ala Met Gly Met Leu Val Glu
                 85                  90                  95

Met Val Asp Lys Lys Gly Pro His Phe Pro Asn Pro Leu Arg Ser Pro
            100                 105                 110

Asp Asp Gly Gln Tyr Ala Ala Leu Met Gln Arg Thr Val Asp Val Ala
        115                 120                 125

Thr Glu Leu Asp Tyr Val Tyr Lys Ala Ile Thr Leu Thr Arg Lys Lys
    130                 135                 140

Leu Gln Gly Arg Val Pro Leu Phe Gly Phe Cys Gly Ala Pro Trp Thr
145                 150                 155                 160

Leu Phe Cys Tyr Met Val Glu Gly Gly Thr Lys Leu Phe Lys Glu
                165                 170                 175

Ser Lys Thr Trp Ile Tyr Lys Tyr Pro Glu Glu Thr Lys Ala Leu Leu
            180                 185                 190

Gln Lys Ile Ser Glu Leu Cys Val Glu Tyr Leu Ala Leu Gln Val Lys
        195                 200                 205

Ala Gly Ala Gln Ile Ile Gln Val Phe Asp Ser Trp Ala Gly Glu Leu
    210                 215                 220

Ser Pro Ser Ser Phe Lys Lys Phe Ser Gln Pro Tyr Leu Ala Tyr Ile
225                 230                 235                 240

Ala Gln His Leu Pro Ala Arg Leu Lys Gln Met Gly Leu Glu Pro Val
                245                 250                 255

Pro Met Val Val Phe Pro Lys Gly Ala Trp Tyr Ala Leu Asp Ala Ala
            260                 265                 270

Cys Asp Met Gly Tyr Asn Val Val Ser Leu Asp Trp Leu His Asp Pro
        275                 280                 285

Ala Asp Ala Val Lys Val Val Gly Asp Arg Pro Val Val Leu Gln Gly
    290                 295                 300

Asn Ala Asp Pro Gly Val Leu Tyr Gly Ser His Ala Ala Ile Thr Glu
305                 310                 315                 320

Ala Val Ala Glu Met Val Lys Gly Phe Gly Trp Pro Asp Arg Lys Lys
                325                 330                 335
```

-continued

```
Gly Trp Ile Val Asn Leu Gly His Gly Ile Thr Pro Phe Val Asn Pro
            340                 345                 350

Asp Asp Leu Lys Phe Phe Phe Gln Glu Ile His Arg Leu Thr Lys Thr
        355                 360                 365

Asp Gly Gln
    370

<210> SEQ ID NO 3
<211> LENGTH: 19
<212> TYPE: DNA
<213> ORGANISM: Thielavia

<400> SEQUENCE: 3
gtcgccctct tcattcaag                                             19

<210> SEQ ID NO 4
<211> LENGTH: 21
<212> TYPE: DNA
<213> ORGANISM: Thielavia

<400> SEQUENCE: 4
gtaccataca ttccgctctc g                                          21
```

POLYPEPTIDES HAVING UROPORPHYRINOGEN DECARBOXYLASE ACTIVITY AND NUCLEIC ACIDS ENCODING SAME

CROSS-REFERENCE TO RELATED APPLICATIONS

This application claims benefit to provisional application Serial No. 60/065,901, filed on Nov. 17, 1997 (now abandoned), which application is fully incorporated herein by reference.

BACKGROUND OF THE INVENTION

1. Field of the Invention

The present invention relates to isolated polypeptides having uroporphyrinogen decarboxylase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps. The fifth enzyme in the biosynthetic pathway is uroporphyrinogen decarboxylase which catalyzes four step-wise decarboxylations of uroporphyrinogen III to form coproporphyrinogen III.

The conversion of an apoprotein into a hemoprotein depends on the availability of heme provided by the heme biosynthetic pathway. The apoprotein form of the hemoprotein combines with heme to produce the active hemoprotein. The active hemoprotein acquires a conformation which makes the hemoprotein more stable than the apoprotein to proteolytic attack. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by *Aspergillus oryzae* (WO 93/19195). While heme supplementation of a fermentation medium results in a significant improvement in the yield of a hemoprotein, it is non-kosher, costly, and difficult to implement on a large scale.

The overexpression of a gene in the heme biosynthetic pathway of a cell provides an alternative approach for overcoming this problem.

Uroporphyrinogen decarboxylase (also called uro D or uroporphyrinogen III decarboxylase) catalyzes the decarboxylation of all four acetic acid side chains of uroporphyrinogen III to methyl groups to yield coproporphyrinogen III. Uroporphyrinogen decarboxylase genes have been cloned from *Saccharomyces cerevisiae* (Garey et al., 1992, *European Journal of Biochemistry* 205:1011–1016; Diflumeri et al., 1993, *Yeast* 9: 613–623); *Bacillus subtilis* (Hansson and Hederstedt, 1992, *Journal of Bacteriology* 174: 8081–8093); *Escherichia coli* (Nishimura et al., 1993, *Gene* 133: 109–113); *Synechococcus* sp. (Kiel et al., 1992, *DNA Seq.* 2: 415–418); *Rhodobacter capsulatus* (Ineichen and Biel, 1995, *Plant Physiology* 108: 423); human (Romeo et al., 1986, *Journal of Biological Chemistry* 261:9825–9831); and mouse (Wu et al., 1996, *Mammalian Genome* 7: 349–352).

It is an object of the present invention to provide improved polypeptides having uroporphyrinogen decarboxylase activity and genes encoding same.

SUMMARY OF THE INVENTION

The present invention relates to isolated polypeptides having uroporphyrinogen decarboxylase activity selected from the group consisting of:

(a) a polypeptide having an amino acid sequence which has at least 65% identity with the amino acid sequence of SEQ ID NO:2;

(b) a polypeptide encoded by a nucleic acid sequence which hybridizes under medium stringency conditions with (i) the nucleic acid sequence of SEQ ID NO:1 or (ii) its complementary strand; or a subsequence thereof of at least 100 nucleotides;

(c) an allelic variant of (a) or (b); and (d) a fragment of (a), (b) or (c), wherein the fragment has uroporphyrinogen decarboxylase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIGS. 1A–1E show the nucleic acid sequence and the deduced amino acid sequence of a *Thielavia terrestris* NRRL 8126 uroporphyrinogen decarboxylase (SEQ ID NOS:1 and 2, respectively).

DETAILED DESCRIPTION OF THE INVENTION

Polypeptides Having Uroporphyrinogen Decarboxylase Activity

The term "uroporphyrinogen decarboxylase activity" is defined herein as a decarboxylase activity which catalyzes the decarboxylation of all four acetic acid side chains of uroporphyrinogen III to methyl groups to yield coproporphyrinogen III. For purposes of the present invention, uroporphyrinogen decarboxylase activity is determined according to the procedure described by Straka et al., 1982, *Enzyme* 28: 170–185; or Felix and Brouillet, 1990, *European Journal of Biochemistry* 188: 393–403.

In a first embodiment, the present invention relates to isolated polypeptides having an amino acid sequence which has a degree of identity to the amino acid sequence of SEQ ID NO:2 of at least about 65%, preferably at least about 70%, more preferably at least about 80%, even more preferably at least about 90%, most preferably at least about 95%, and even most preferably at least about 97%, which have uroporphyrinogen decarboxylase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two amino acid sequences is determined by the Smith-Waterman algorithm (Smith and Waterman, 1981,

*Nucleic Acids Research* 10: 197–206) using the GeneAssist™ software program FDF Smith-Waterman with the amino acid scoring matrix BLOSUM 62 (Applied Biosystems, Inc., Foster City, Calif.) with rescoring and normalization on all scores above 30.

Preferably, the polypeptides of the present invention comprise the amino acid sequence of SEQ ID NO:2, or an allelic variant thereof; or a fragment thereof, wherein the fragment has uroporphyrinogen decarboxylase activity. In a more preferred embodiment, the polypeptides of the present invention comprise the amino acid sequence of SEQ ID NO:2. In another preferred embodiment, the polypeptide of the present invention consists of the amino acid sequence of SEQ ID NO:2 or an allelic variant thereof; or a fragment thereof, wherein the fragment has uroporphyrinogen decarboxylase activity. In a more preferred embodiment, the polypeptide of the present invention consists of the amino acid sequence of SEQ ID NO:2.

A fragment of SEQ ID NO:2 is a polypeptide having one or more amino acids deleted from the amino and/or carboxyl terminus of this amino acid sequence. Preferably, a fragment contains at least 310 amino acid residues, more preferably at least 330 amino acid residues, and most preferably at least 350 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having uroporphyrinogen decarboxylase activity which are encoded by nucleic acid sequences which hybridize under low stringency conditions, more preferably medium stringency conditions, even more preferably high stringency conditions, and most preferably very high stringency conditions, with a nucleic acid probe which hybridizes under the same conditions with the nucleic acid sequence of SEQ ID NO:1 or its complementary strand; or a subsequence thereof which encodes a polypeptide fragment which has uroporphyrinogen decarboxylase activity (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO:1 may be at least 100 nucleotides or preferably at least 200 nucleotides. Moreover, the subsequence may encode a polypeptide fragment which has uroporphyrinogen decarboxylase activity. The polypeptides may also be allelic variants or fragments of the polypeptides, wherein the fragments have uroporphyrinogen decarboxylase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having uroporphyrinogen decarboxylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having uroporphyrinogen decarboxylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, the carrier material is used in a Southern blot. For purposes of the present invention, hybridization indicates that the nucleic acid sequence hybridizes to a nucleic acid probe corresponding to the nucleic acid sequence shown in SEQ ID NO:1, its complementary strand, or a subsequence thereof, under low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the nucleic acid sequence contained in plasmid pSE61 which is contained in *Escherichia coli* NRRL B-21884, wherein the nucleic acid sequence encodes the polypeptide of SEQ ID NO:2.

For long probes of at least 100 nucleotides in length, low to high stringency conditions are defined as prehybridization and hybridization at 42° C. in 5× SSPE, 0.3% SDS, 200 µg/ml sheared and denatured salmon sperm DNA, and either 25, 35 or 50% formamide for low, medium and high stringencies, respectively, following standard Southern blotting procedures.

For long probes of at least 100 nucleotides in length, the carrier material is finally washed three times each for 15 minutes using 2× SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6× SCC plus 0.1% SDS for 15 minutes and twice each for 15 minutes using 6× SSC at 5° C. to 10° C. below the calculated $T_m$.

In a third embodiment, the present invention relates to isolated polypeptides having immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A farther explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20% preferably at least 40%, more preferably at least 60%, even more preferably at least 80%, even more preferably at least 90%, and most preferably at least 100% of the uroporphyrinogen decarboxylase activity of SEQ ID NO:2.

A polypeptide of the present invention may be obtained from microorganisms of any genus.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Totypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptides are obtained from a *Thielavia appendiculata, Thielavia achromatica, Thielavia albomyces, Thielavia albopilosa, Thielavia arenaria, Thielavia australiensis, Thielavia basicola, Thielavia coactilis, Thielavia fimeti, Thielavia fragilis, Thielavia heterothallica, Thielavia hyrcaniae, Thielavia inaequalis, Thielavia kuwaitensis, Thielavia microspora, Thielavia minor, Thielavia minuta, Thielavia novoguineensis, Thielavia ovata, Thielavia ovispora, Thielavia pallidospora, Thielavia peruviana, Thielavia sepedonium, Thielavia setosa, Thielavia setosus, Thielavia subthermophila, Thielavia tanzanica, Thielavia terrestris, Thielavia terricola, Thielavia thermophila, Thielavia variospora,* or *Thielavia wareingii* strain.

In a more preferred embodiment, a polypeptide of the present invention is obtained from a *Thielavia terrestris* strain, and most preferably from *Thielavia terrestris* NRRL 8126 or a mutant strain thereof, e.g., the polypeptide with the amino acid sequence of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, the polypeptides may be obtained from microorganisms which are taxonomic equivalents of Thielavia as defined by Von Arx, 1995, *Studies in Mycology* 8: 1–29, regardless of the species name by which they are known. For instance, the imperfect form of *Thielavia terrestris* is known as *Acremonium alabamese*, and *Myceliophthora thenmophila* is *Thielaia heterothallica*.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-uroporphyrinogen decarboxylase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pSE61 which is contained in *Escherichia coli* NRRL B-21884. The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 which have uroporphyrinogen decarboxylase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 990 nucleotides, more preferably at least 1140 nucleotides, and most preferably at least 1290 nucleotides.

The present invention also relates to mutant nucleic acid sequences comprising at least one mutation in the nucleic acid sequence of SEQ ID NO:1, in which the mutant nucleic acid sequence encodes a polypeptide having the amino acid sequence of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Thielavia, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the nucleic acid sequence of SEQ ID NO:1 of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the FAST algorithm (Dumas and Ninio, 1981, *Nucleic Acids Research* 10: 197–206) using the GeneAssist™ software program FASTA (Applied Biosystems, Inc., Foster City, Calif.) with a ktup size of 5 and a dna.mat matrix.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability., pH optimum, or the like using, e.g., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for uroporphyrinogen decarboxylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under low stringency conditions, more preferably medium stringency conditions, even more preferably high stringency conditions, and most preferably very high stringency conditions, with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA with the sequence of SEQ ID NO:1, or its complementary strand, or a subsequence thereof which encodes a polypeptide fragment which has uroporphyrinogen decarboxylase activity, under low, medium, high, or very high stringency conditions; and (b) isolating the nucleic acid sequence.

Methods for Producing Mutant Nucleic Acid Sequences

The present invention further relates to methods for producing a mutant nucleic acid sequence, comprising introducing at least one mutation into the nucleic acid sequence of SEQ ID NO:1 or a subsequence thereof, wherein the mutant nucleic acid sequence encodes a polypeptide having an amino acid sequence of SEQ ID NO:2 or a fragment thereof which has uroporphyrinogen decarboxylase activity.

The introduction of a mutation into the nucleic acid sequence to switch one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The nucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the E. coli lac operon, the Streptomyces coelicolor agarase gene (dagA), the Bacillus subtilis levansucrase gene (sacB), the Bacillus licheniformis alpha-amylase gene (amyL), the Bacillus stearothermophilus maltogenic amylase gene (amyM), the Bacillus amyloliquefaciens alpha-amylase gene (amyQ), the Bacillus licheniformis penicillinase gene (penP), the Bacillus subtilis xylA and xylB genes, and the prokaryotic beta-lactamase gene (Villa-Kamaroff et al., 1978, Proceedings of the National Academy of Sciences USA 75: 3727–3731), as well as the tac promoter (DeBoer et al., 1983, Proceedings of the National Academy of Sciences USA 80: 21–25). Further promoters are described in "Useful proteins from recombinant bacteria" in Scientific American, 1980, 242: 74–94; and in Sambrook et al., 1989, supra.

Examples of suitable promoters for directing the transcription of the nucleic acid constructs of the present invention in a filamentous fungal host cell are promoters obtained from the genes encoding Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, Fusarium oxysporum trypsin-like protease (WO 96/00787), NA2-tpi (a hybrid of the promoters from the genes encoding Aspergillus niger neutral alpha-amylase and Aspergillus oryzae triose phosphate isomerase), and mutant, truncated, and hybrid promoters thereof.

In a yeast host, useful promoters are obtained from the Saccharomyces cerevisiae enolase (ENO-1) gene, the Saccharomyces cerevisiae galactokinase gene (GAL1), the Saccharomyces cerevisiae alcohol dehydrogenase/glyceraldehyde-3-phosphate dehydrogenase genes (ADH2/GAP), and the Saccharomyces cerevisiae 3-phosphoglycerate kinase gene. Other useful promoters for yeast host cells are described by Romanos et al., 1992, Yeast 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding Aspergillus oryzae TAKA amylase, Aspergillus niger glucoamylase, Aspergillus nidulans anthranilate synthase, Aspergillus niger alpha-glucosidase, and Fusarium oxysporum trypsin-like protease.

Preferred terminators for yeast host cells are obtained from the genes encoding Saccharomyces cerevisiae enolase, Saccharomyces cerevisiae cytochrome C (CYC1), or Saccharomyces cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes encoding Aspergillus oryzae TAKA amylase and Aspergillus nidulans triose phosphate isomerase.

Suitable leaders for yeast host cells are obtained from the Saccharomyces cerevisiae enolase (ENO-1) gene, the Saccharomyces cerevisiae 3-phosphoglycerate kinase gene, the Saccharomyces cerevisiae alpha-factor, and the Saccharomyces cerevisiae alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding Aspergillus oryzae TAKA amylase, Aspergillus niger glucoamylase, Aspergillus nidulans anthranilate synthase, Fusarium oxysporum trypsin-like protease, and Aspergillus niger alpha-glucosidase.

Useful polyadenylation sequences for yeast host cells are described by Guo and Sherman, 1995, Molecular Cellular Biology 15: 5983–5990.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the Bacillus stearothermophilus alpha-amylase gene, the Bacillus licheniformis subtilisin gene, the Bacillus licheniformis beta-lactamase gene, the Bacillus stearothermophilus neutral proteases genes (nprT, nprS, nprM), or the Bacillus subtilis prsA gene. Further signal peptides are described by Simonen and Palva, 1993, Microbiological Reviews 57: 109–137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, Humicola insolens cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (npr7), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents from other species. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E.* coli and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian cell, an insect cell, a plant cell or a fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Totypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophila* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Thielavia, and more preferably *Thielavia terrestris*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence of SEQ ID NO:1 having at least one mutation in the nucleic acid sequence of SEQ ID NO:1, wherein the mutant nucleic acid sequence encodes a polypeptide having an amino acid sequence of SEQ ID NO:2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670. Gene activation technology is based on activating a gene which is normally unexpressed in a cell or increasing expression of a gene which is expressed at very low levels in a cell. Gene activation technology includes methods of inserting an exogenous DNA construct containing a regulatory sequence, an exon, and/or a splice donor site into the genomic DNA of a cell in such a manner that the insertion results in the production of a new transcription unit in which the regulatory sequence, the exon, and/or the splice donor site are operably linked to and activate expression of the endogenous gene.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining uroporphyrinogen decarboxylase activity are known in the art. As described earlier, uroporphyrinogen decarboxylase activity is determined according to the procedure described by Straka et al., 1982, *Enzyme* 28: 170–185; or Felix and Brouillet, 1990, *European Journal of Biochemistry* 188: 393–403.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Uses

The present invention is also directed to methods for using the polypeptides having uroporphyrinogen decarboxylase activity.

The polypeptides of the present invention may be used to increase the yield of a hemoprotein produced by a host cell, where uroporphyrinogen decarboxylase activity is a rate-limiting step in the production of heme in the host cell, by overexpressing the nucleic acid sequence encoding the polypeptide having uroporphyrinogen decarboxylase activity in the host cell. The method comprises: (a) introducing into the host cell, which is capable of producing the hemoprotein, one or more copies of the nucleic acid sequence encoding the polypeptide having uroporphyrinogen decarboxylase activity, wherein the nucleic acid sequence is operably linked to regulatory regions capable of directing the expression of the polypeptide; (b) cultivating the cell in a nutrient medium suitable for production of the hemoprotein and the polypeptide; and (c) recovering the hemoprotein from the nutrient medium of the cell (see WO 97/47746).

The present invention may also be used for the production of heterologous polypeptides. The method comprises (a) introducing into a respiratory-defective mutant of a cell a nucleic acid construct comprising a first nucleic acid sequence encoding a polypeptide of the present invention and a second nucleic acid sequence, wherein the first nucleic acid sequence upon expression complements the respiratory defect and the second nucleic acid sequence encodes a heterologous polypeptide; (b) cultivating the cell containing the first and second nucleic acid sequences in a culture medium under aerobic conditions suitable for expression of the first and second nucleic acid sequences; and (c) recovering the heterologous polypeptide (see WO 98/41640).

The present invention is further described by the following examples which should not be construed as limiting the scope of the invention.

EXAMPLES

Example 1

*Thielavia terrestris* cDNA Library Construction

Spores of *Thielavia terrestris* E373 (NRRL 8126) were germinated at pH 5.0 and 44° C. in a 2 liter fermentation containing medium composed of per liter 2.0 g of $MgSO_4 \cdot 7H_2O$, 5.0 g of $KH_2PO_4$, 4.0 g of citric acid, 10.0 g of yeast extract, 10.0 g of $(NH_4)_2SO_4$, 2.0 g/l $CaCl_2$, 0.5 ml of trace metals solution, 1.0 ml of pluronic, and 200 g of glucose. The trace metals solution (100×) was composed per liter of 22 g of $ZnSO_4 \cdot 7H_2O$, 11 g of $H_3BO_3$, 5 g of $MnCl_2 \cdot 4H_2O$, 5 g of $FeSO_4 \cdot 7H_2O$, 1.6 g of $CoCl_2 \cdot 5H_2O$, 1.6 g of $(NH_4)_6Mo_7O_{24}$, and 50 g of $Na_4EDTA$.

Total RNA was isolated from 2 grams of mycelia harvested just before sporulation according to the procedure of Wahleithner et al., 1996, *Current Genetics* 29: 395–403. Purification of the mRNA from the total RNA was performed using Oligotex-dT™ (Qiagen, Chatsworth, Calif.) as recommended by the manufacturer.

Double-stranded cDNA was synthesized from 5 µg of *Thielavia terrestris* NRRL 8126 poly(A)+ RNA as described by Gubler and Hoffman (1983, *Gene* 25: 263–269) and Sambrook et al. (1989, *Molecular Cloning: A Laboratory Manual*, Cold Spring Harbor Press, Cold Spring Harbor, N.Y.), except that an oligo(dT)-NotI anchor primer, instead of an oligo(dT)12-18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated into λZiplox™ EcoRI arms according to the manufacturer's instructions (Gibco BRL, Gaithersburg, Md.) and packaged in vitro into phage particles with the Gigapack Gold™ kit (Stratagene, La Jolla, Calif.).

Example 2

DNA Analysis of "Tagged" Random cDNA Clones

DNA sequencing was determined using Prizm™ dye terminator chemistry run on an Applied Biosystems 373 DNA Sequencer (Applied Biosystems, Inc., Foster City, Calif.) according to the manufacturer's instructions. Forward and reverse universal primers were use to "tag" the randomly picked cDNA clones.

DNA sequence "tags" of the random cDNA clones were first analyzed by Factura™ (Applied Biosystems, Inc., Foster City, Calif.) to automatically inactivate vector sequences and inactivate polyA tails so as to not be included in further analysis. Comparisons of deduced amino acid sequences to protein databases were determined by the Smith-Waterman algorithm (Smith and Waterman, 1981, *Nucleic Acids Research* 10: 197–206) using the GeneAssist™ software program FDF Smith-Waterman with the amino acid scoring matrix BLOSUM 62 (Applied Biosystems, Inc., Foster City, Calif.) with rescoring and normalization on all scores above 30.

The deduced amino acid sequence of one clone showed similarity to the *Saccharomyces cerevisiae* uroporphyrinogen decarboxylase gene. The cDNA fragment contained 531 nucleotides.

Example 3

*Thielavia terrestris* Genomic DNA Extraction

*Thielavia terrestris* NRRL 8126 was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3 M solution) was added to a final concentration of 0.3 M followed by addition of 2.5 volumes of ice cold ethanol to precipitate the nucleic acids. The nucleic acids were then pelleted by centrifuging the tube at 15,000× g for 30 minutes. The pellet was allowed to air dry for 30 minutes before resuspension in 0.5 ml of TE buffer. DNase-free ribonuclease A was added to a concentration of 100 mg/ml and the mixture was incubated at 37° C. for 30 minutes. Proteinase K was then added at a concentration of 200 mg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 4

*Thielavia terrestris* Genomic DNA Libraries and Identification of Uroporphyrinogen Decarboxylase (hemE) Clones A full length genomic clone of a uroporphyrinogen decarboxylase gene was isolated from a *Thielavia terrestris* genomic DNA library using the partial *Thielavia terrestris* hemE cDNA described in Example 2 as a probe.

The DNA probe was made by PCR amplification of the *Thielavia terrestris* cDNA clone using primers TtUroD-PCR1 5'-GTCGCCCTCTTCATTCAAG-3' (SEQ ID NO:3) and TtUroDPCR2 5'-GTACCATACATTCCGCTCTCG-3' (SEQ ID NO:4) and the hemE partial cDNA as template. The amplification reaction contained the following components: 0.5 μg of hemE partial cDNA, 100 μM each of dATP, dCTP, dGTP, and dTTP, 50 pmoles each of primer TtUroDPCR1 and primer TtUroDPCR2, 2 units of Taq DNA polymerase, and 1× Taq DNA polymerase buffer. The reaction was incubated in a Perkin-Elmer Thermal Cycler programmed for 30 cycles each at 95° C. for 1 minute, 55° C. for 1 minute, and 72° C. for 2 minutes.

The ~500 bp DNA fragment was gel purified and further purified using a QiaQuick spin column (Qiagen, Chatsworth, Calif.). The DNA fragment was then radioactively-labeled using [α-$^{32}$P]dCTP and the Prime-It II Random Priming kit (Stratagene, La Jolla, Calif.).

A *Thielavia terrestris* genomic DNA library was constructed using the bacteriophage cloning vector λZipLox (Gibco BRL, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Genomic DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 3–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged in vitro into phage particles using the Gigapack Gold kit according to the manufacturer's (Stratagene, La Jolla, Calif.). The packaged DNA libraries were plated and amplified in *E. coli* Y1090ZL cells. The unamplified genomic library contained 1×10$^6$ pfu/ml.

Approximately 120,000 plaques were lifted onto duplicate Hybond N+ filters (Amersham, Arlington Heights, Ill.) and prehybridized using Rapid Hyb (Amersham, Arlington Heights, Ill.) for two hours at 65° C. Hybridization with 1×10$^7$ cpm of denatured hemE probe was performed in 100 ml of Rapid Hyb for three hours at 65° C. Filters were washed twice at room temperature in a solution containing 2× SSC-0.1% SDS followed by two washes at 65° C. for 15 minutes in a solution containing 0.5× SSC-0.1% SDS. The filters were then rinsed in 2× SSC and autoradiographed using Kodak X-OMAT AR film for approximately 2 hours at room temperature followed by development using a Konica QX-70 automatic film processor according to the manufacturer's instructions. Primary plaques were purified and screened a second time.

Five positive clones were identified and excised into pZL derivatives according to the manufacturer's instructions (Bethesda Research Laboratories, Inc., Gaithersburg, Md.). The pZL derivatives were designated *E. coli* DH5a pSE61, pSE62, pSE63, pSE64, and pSE65. Restriction mapping of the clones revealed that pSE62 and pSE63 were similar and that pSE61 contained the largest insert (approximately 4 kb). pSE61 was used for sequence analysis.

Example 5

Characterization of *Thielavia terrestris* Uroporphyrinogen Decarboxylase (hemE) Gene

*E. coli* DH5a pSE61 described in Example 2 was subjected to DNA sequencing according to the following procedure. DNA sequencing was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38:47–60) using the M13 reverse (−48) and M13 forward (−20) primers (New England Biolabs, Beverly, Mass.) and primers unique to the DNA being sequenced.

The nucleotide sequence of the cloned gene revealed an open reading frame (ORF) of 1410 nucleotides as shown in FIG. 1 (SEQ ID NO:1). Within the 1410 bp ORF was found four introns ranging in size from 50 to 114 nucleotides located at positions 58, 215, 816 and 1272. The hemE gene contained an average GC content of 56.8%. However, the exons contained higher GC content than the introns, while the GC content of the introns was more variable. The GC content of exons 1, 2, 3, 4, and 5 was 60.3%, 71.4%, 58.9%, 59.4%, and 51.8%, respectively. The GC content of introns 1, 2, 3, and 4 was 32.2%, 69.2%, 47.2%, and 58.8%, respectively. The average GC content of the five exons was 60.4%±6.3% and the intron average was 51.8%±13.8%.

The deduced amino acid sequence of the *Thielavia terrestris* gene product is shown in FIG. 1 (SEQ ID NO:2). The open reading frame of 1113 bp nucleotide sequence encodes a predicted protein of 371 amino acids with a molecular weight of approximately 50 kDa.

Overall, the deduced amino acid sequence of the *Thielavia terrestris* uroporphyrinogen decarboxylase shared 57% and 44% identity with the amino acid sequences of the uroporphyrinogen decarboxylases from *Saccharomyces cerevisiae* (Garey et al., 1992, *European Journal of Biochemistry* 205:1011–1016); and human (Romeo et al., 1986, *Journal of Biological Chemistry* 261:9825–9831), respectively, as determined by the Smith-Waterman algorithm (Smith and Waterman, 1981, *Nucleic Acids Research* 10: 197–206) using the GeneAssist™ software program FDF Smith-Waterman with the amino acid scoring matrix BLOSUM 62 (Applied Biosystems, Inc., Foster City, Calif.) with rescoring and normalization on all scores above 30.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* DH5a pSE61 | NRRL B-21884 | November 14, 1997 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having uroporphyrinogen decarboxylase activity, selected from the group consisting of:
    (a) a polypeptide having an amino acid sequence which has at least 80% identity with the amino acid sequence of SEQ ID NO:2;
    (b) a polypeptide which is encoded by a nucleic acid sequence which hybridizes under high stringency conditions with (i) the nucleic acid sequence of SEQ ID NO:1 or (ii) its complementary strand; and
    (c) a fragment of (a), or (b), wherein the fragment has uroporphyrinogen decarboxylase activity.

2. The polypeptide of claim 1, having an amino acid sequence which has at least 80% identity with the amino acid sequence of SEQ ID NO:2.

3. The polypeptide of claim 2, having an amino acid sequence which has at least 90% identity with the amino acid sequence of SEQ ID NO:2.

4. The polypeptide of claim 3, having an amino acid sequence which has at least 95% identity with the amino acid sequence of SEQ ID NO:2.

5. The polypeptide of claim 1, comprising the amino acid sequence of SEQ ID NO:2.

6. The polypeptide of claim 1, consisting of the amino acid sequence of SEQ ID NO:2 or a fragment thereof.

7. The polypeptide of claim 6, consisting of the amino acid sequence of SEQ ID NO:2.

8. The polypeptide of claim 2, which is obtained from a Thielavia strain.

9. The polypeptide of claim 8, which is obtained from Thielavia terrestris strain.

10. The polypeptide of claim 1, which is encoded by a nucleic acid sequence which hybridizes under high stringency conditions with the nucleic acid sequence of SEQ ID NO:1 or its complementary strand.

11. The polypeptide of claim 10, which is obtained from a Thielavia strain.

12. The polypeptide of claim 11, which is obtained from Thielavia terrestris strain.

13. The polypeptide of claim 1, which is encoded by a nucleic acid sequence which hybridizes under very high stringency conditions with the nucleic acid sequence of SEQ ID NO:1 or its complementary strand.

14. The polypeptide of claim 13, which is obtained from a Thielavia strain.

15. The polypeptide of claim 14, which is obtained from Thielavia terrestris strain.

16. The polypeptide of claim 1, which is encoded by the nucleic acid sequence contained in plasmid pSE61 contained in E. coli NRRL B-21884.

17. The polypeptide of claim 1 which has at least 20% of the uroporphyrinogen decarboxylase activity of SEQ ID NO:2.

* * * * *